(12) United States Patent
Ronchi et al.

(10) Patent No.: US 11,723,942 B2
(45) Date of Patent: Aug. 15, 2023

(54) POWDER SOLID COMPOSITIONS, PROCESS FOR THEIR PREPARATION, FORMULATIONS AND USE THEREOF

(71) Applicant: INDENA S.P.A., Milan (IT)

(72) Inventors: Massimo Ronchi, Milan (IT); Giacomo Mombelli, Milan (IT)

(73) Assignee: INDENA S.P.A., Milan (IT)

( * ) Notice: Subject to any disclaimer, the term of this patent is extended or adjusted under 35 U.S.C. 154(b) by 363 days.

(21) Appl. No.: 16/466,846

(22) PCT Filed: Nov. 29, 2017

(86) PCT No.: PCT/EP2017/080866
§ 371 (c)(1),
(2) Date: Jun. 5, 2019

(87) PCT Pub. No.: WO2018/104131
PCT Pub. Date: Jun. 14, 2018

(65) Prior Publication Data
US 2020/0061143 A1 Feb. 27, 2020

(30) Foreign Application Priority Data
Dec. 6, 2016 (EP) .................................. 16202405

(51) Int. Cl.
| | | |
|---|---|---|
| *A61K 36/752* | (2006.01) | |
| *A23L 33/105* | (2016.01) | |
| *A61K 9/14* | (2006.01) | |
| *A61K 9/16* | (2006.01) | |
| *A61K 9/20* | (2006.01) | |
| *A61K 9/48* | (2006.01) | |
| *A61K 31/7048* | (2006.01) | |
| *A23P 10/40* | (2016.01) | |
| *A61P 3/06* | (2006.01) | |

(52) U.S. Cl.
CPC .......... *A61K 36/752* (2013.01); *A23L 33/105* (2016.08); *A23P 10/40* (2016.08); *A61K 9/145* (2013.01); *A61K 9/1617* (2013.01); *A61K 9/1641* (2013.01); *A61K 9/1652* (2013.01); *A61K 9/1694* (2013.01); *A61K 9/2009* (2013.01); *A61K 9/2013* (2013.01); *A61K 9/2054* (2013.01); *A61K 9/485* (2013.01); *A61K 9/4858* (2013.01); *A61K 31/7048* (2013.01); *A61P 3/06* (2018.01); *A23V 2002/00* (2013.01)

(58) Field of Classification Search
CPC .......................... A61K 36/752; A61K 31/7048
See application file for complete search history.

(56) References Cited

U.S. PATENT DOCUMENTS

| 8,741,362 B2 * | 6/2014 | Lombardo | .............. A61P 17/00 424/736 |
| 2011/0223271 A1 * | 9/2011 | Lombardo | ................ A61P 3/06 424/777 |

FOREIGN PATENT DOCUMENTS

| CN | 1772011 A | 5/2006 | |
| CN | 105982926 A | 10/2016 | |
| EP | 2149377 A1 * | 2/2010 | ............. A61K 36/29 |
| JP | S63-198693 A | 8/1988 | |
| WO | WO-2010055490 A2 * | 5/2010 | .......... A61K 36/752 |
| WO | WO-2013003670 A1 * | 1/2013 | ............. A23L 29/10 |

OTHER PUBLICATIONS

Dugo et al., "Citrus bergamia: bergamot and its derivatives". CRC Press: Boca Raton. 2014, p. 31. (Year: 2014).*
Nogata et al. Biosci. Biotechnol. Biochem., 70 (1), 178-192, 2006. (Year: 2006).*
Kato-Kataoka et al. J Clin Biochem Nutr. Nov. 2010; 47(3): 246-255. (Year: 2010).*
Gurr et al. found in the chapter titled "Biodiversity of Plant Resource of Insect Control Compounds": "Sugar esters" and "Phytochemicals from Essential Oils". John-Wiley and Sons, Blackwell: Hoboken. 2012, 7 pages. (Year: 2012).*
Semalty A, et al "Supramolecular Phospholipids-Polyphenolics Interactions: The PHYTOSOME® Strategy to Improve the Bioavailability of Phytochemicals" Fitoterapia, 81(5),Jul. 1, 2010, 306-314; XP055030955; ISSN: 0367-326X; doi:10.1015/j.fitote.2009.11.001. (Year: 2010).*
Losio et al., "Oral bioavailability of silymarin phytocomplex formulated as self-emulsifying pellets," Phytomedicine, vol. 18, 2011, pp. 505-512.
International Search Report, PCT/EP2017/080866, dated Mar. 2, 2018.
Written Opinion, PCT/EP2017/080866, dated Mar. 2, 2018.

* cited by examiner

Primary Examiner — Aaron J Kosar
Assistant Examiner — Amy L Clark
(74) Attorney, Agent, or Firm — Nixon & Vanderhye

(57) ABSTRACT

Disclosed are powder solid compositions including a hydroalcoholic extract of Bergamot fruit (*Citrus aurantium* var. *bergamia*) and at least one phospholipid. Also disclosed is a process for the preparation of the compositions. The compositions are useful for the prevention and/or treatment of dysmetabolic syndromes, dyslipidemias and type 2 diabetes.

8 Claims, No Drawings

POWDER SOLID COMPOSITIONS, PROCESS FOR THEIR PREPARATION, FORMULATIONS AND USE THEREOF

TECHNICAL FIELD OF THE INVENTION

The present invention relates to powder solid compositions comprising an extract of Bergamot and phospholipids.

The invention also relates to a process for the preparation of said compositions in form of powder solid. Furthermore, the invention concerns pharmaceutical, nutraceutical and cosmetic formulations comprising said compositions as well as the use of said compositions and formulations.

BACKGROUND OF THE INVENTION

Flavonoids are an important family of polyphenolic compounds naturally occurring in fruit and vegetables.

The positive effect of flavonoids in the prevention and amelioration of metabolic syndrome and in the treatment of associated pathologies, like cardiovascular diseases, hyperlipidemia and type 2 diabetes, has been confirmed by several studies (Galleano M. et al. "Flavonoids and metabolic syndrome", Ann. NY Acad. Sci. (2012); 1259: 87-94).

Citrus fruits are an important source of flavonoids. The most important flavonoids of citrus fruits include diosmetin, diosmin, hesperidin, naringin, neohesperidin, nobiletin, quercetin, rutin and the flavone tangeritin. The potential beneficial effects of citrus fruits flavonoids in the treatment of dysmetabolic syndromes, in the normalization of dyslipidemias and in the management of type 2 diabetes is well documented (Ashraful Alam M. et al. "*Effect of Citrus Flavonoids, Naringin and Naringenin on Metabolic Syndrome and Their Mechanisms of Action*", Adv. Nutr. (2014), vol. 5: 404-417; Assini et al. "*Citrus flavonoids in lipid metabolism*", Curr. Opin. Lipidol. (2013), vol. 24(1): 34-40; Un Ju Jung et al., "*Effect of citrus flavonoids on lipid metabolism and glucose-regulating enzyme mRNA levels in type-2 diabetic mice*", Int. J. Biochem. Cell. Biol. (2006), vol. 38(7), 1134-145).

Among the citrus fruits, bergamot represents an important source of specific flavanon-7-O-glycosides, such as naringin, neohesperidin, brutelidin and melitidin, that cannot be found in any other citrus fruits, which have demonstrated potential health benefits in clinical testing (Mollace V., et al. "*Hypolipemic and hypoglycaemic activity of bergamot polyphenols: From animal models to human studies*", Fitoterapia (2011), 3: 309-316).

Recently an hydroalcoholic extract of Bergamot fruit has been developed by Lombardo et al. (U.S. Pat. No. 8,741,362 B2) with a specific polyphenol composition which proved to be effective in reducing cholesterol, blood glucose and treating metabolic syndrome.

As for all the other flavonoids, flavanones-7-O-glycosides of bergamot fruit extracts are characterized by poor oral bioavailability; consequently, high oral doses of bergamot fruit extracts are required to obtain significant health benefits.

Therefore, there is still the need to find alternative Bergamot fruit extract derivatives having improved oral bioavailability.

SUMMARY OF THE INVENTION

The present invention relates to a process for the preparation of powder solid compositions comprising the following steps:

a) a hydroalcoholic extract of Bergamot fruit is dispersed in at least one organic solvent and kept under mixing until a solution or a dispersion is obtained; heating is optionally applied;

b) at least one phospholipid is then added to the solution, or dispersion, of the extract and the mixture is kept under mixing; heating is optionally applied;

c) the organic solvent is then removed to obtain the powder composition.

The invention also relates to the powder solid compositions comprising a hydroalcoholic extract of Bergamot fruit (*Citrus aurantium* var. *bergamia*) and at least one phospholipid obtainable by the process of the invention and it also relates to pharmaceutical, nutraceutical and cosmetic formulations comprising said compositions.

The powder compositions according to the invention and the formulations containing said compositions are useful in the prevention and/or treatment of metabolic syndromes, dyslipidemias and type 2 diabetes.

DETAILED DESCRIPTION OF THE INVENTION

The present invention relates to powder solid compositions comprising a hydroalcoholic extract of Bergamot fruit (*Citrus aurantium* var. *bergamia*) and at least one phospholipid obtainable by the process of the invention.

The hydroalcoholic extract of Bergamot fruit is characterized by the presence of three main flavanone-7-O-glycosides: neoeriocitrin, naringin and neohesperidin, that are the main responsible of the biological activity of the extract.

It has been surprisingly found that the compositions according to the present invention are characterized by an improved oral bioavailability of the active ingredients (flavonoids) of the Bergamot fruit extract and, in particular, of the flavanone-7-O-glycosides, in particular naringin and neohesperidin, which were analyzed in the plasma samples of the pharmacokinetic study on rats.

The phospholipid may be selected from the group comprising lecithins from soy, sunflower or egg, phosphatidyl choline, phosphatidyl serine, phosphatidyl ethanolamine, wherein the acyl groups being the same or different are mostly derived from palmitic, stearic, oleic, linoleic, linolenic acids; or combinations thereof. Preferably, the phospholipid is lecithin.

The at least one phospholipid to Bergamot fruit extract flavanone-7-O-glycosides (neoeriocitrin, naringin and neohesperidin) weight ratio is in the range from 6 to 30, preferably from 6 to 20, more preferably from 6 to 12.

Thanks to this ratio an improved oral bioavailability of the active ingredients (flavonoids) of Bergamot fruit extract is achieved.

The powder solid compositions may also comprise an additional surfactant, other than lecithin, with a HLB value equal or higher than 12. This additional surfactant enhances the solubilisation of Bergamot fruit extract in the organic solvent during the manufacturing process and maximizes the interaction of the extract with phospholipids. Furthermore, the additional surfactant enhances the wettability and fast dispersion of the powder solid dispersion in the gut fluids and promotes a faster and higher absorption, hence a higher bioavailability of the active ingredient of Bergamot fruit extract.

The additional surfactant may be selected from the group comprising sucrose esters, polysorbates, polyoxyethylene castor oil derivatives, polyoxyethylene stearates, D-α-tocopheryl polyethylene glycol succinate, or combinations thereof. Sucrose esters and D-α-tocopheryl polyethylene glycol succinate are the preferred ones.

Additional ingredients may be also added to the powder solid dispersion with the purpose to improve its physical and technological characteristics, allowing an easier incorporation in conventional dosage forms, such as tablets and capsules.

These additional ingredients may include soluble and insoluble fillers, such as cellulose powder, microcrystalline cellulose, calcium carbonate, calcium phosphate, mannitol, maltodextrins, sorbitol, xylitol, fructose, isomalt, inulin; binders, such as methylcellulose, hydroxypropylmethyl cellulose, hydroxypropyl cellulose, natural gums; glidants and lubricants, such as silicon dioxide, talc, stearic acid, magnesium stearate.

The present invention also relates to a manufacturing process for the preparation of the powder solid compositions comprising hydroalcoholic Bergamot fruit extract and at least one phospholipid.

The manufacturing process for preparing a powder solid composition according to the present invention comprises the following steps:

a) a hydroalcoholic extract of Bergamot fruit is dispersed in at least one suitable organic solvent and kept under mixing until a solution or a dispersion is obtained; heating is optionally applied, if required;

b) at least one phospholipid is then added to the solution/dispersion of the Bergamot fruit extract and the mixture is kept under mixing; heating is optionally applied;

c) the organic solvent is then removed to obtain the composition in the form of powder solid.

The suitable organic solvent is a polar organic solvent that leads to a total or at least substantial solubilisation of the extract, such as polar protic solvent or a polar aprotic solvent.

Preferably the polar protic solvent is a, straight or branched, $C_1$-$C_8$ alkyl alcohol and the polar aprotic solvent is a, straight or branched, $C_1$-$C_8$ alkyl ester or a $C_1$-$C_8$ dialkylketone.

A total or event partial solubilisation of the phospholipids in the selected organic solvent is also desirable.

The organic solvent may be selected from the group comprising ethyl alcohol, ethyl acetate, acetone, isobutyl alcohol, isopropyl alcohol, and combinations thereof. Ethyl alcohol and ethyl acetate are preferred.

Heating is optionally applied to facilitate solubilisation without causing any degradation of the active ingredients.

After step b) the additional surfactant and/or additional ingredients may be added to the obtained solution (or dispersion), which is kept under mixing for a suitable period of time to facilitate the interaction of the different ingredients.

The solvent may be removed under vacuum. Alternative drying method may also be used to remove the organic solvent, such as spray drying and freeze drying.

The obtained powder composition usually is then calibrated and eventually grinded to obtain the desired particle size distribution.

The present invention also relates to pharmaceutical, nutraceutical and cosmetic formulations comprising a composition of the invention and at least one physiologically acceptable excipient and/or carrier.

Preferably the formulations are for oral administration or for topical administration.

Physiologically acceptable excipients and/or carriers may be, for example, disintegrant, lubricant, binder, coating agent, colorant, absorption enhancer, solubilizing agent, stabilizer, flavor, sweetener, antiseptic, preservative, antioxidant and the like.

Examples of dosage forms of the formulations of the invention may be, for example tablets, chewable tablets, hard gelatin capsules, powder for reconstitution, extemporary or ready-to-use suspensions.

The powder solid compositions of the invention and formulations thereof may be used, alone or in combination with other botanical extracts, for the prevention and/or treatment of dysmetabolic syndromes, dyslipidemias and type 2 diabetes.

The improved bioavailability of active ingredients (flavonoids) of the hydroalcoholic extract of Bergamot fruit allows a significant reduction of the daily dosage and an improvement of the pharmacological performance of Bergamot fruit extract.

The powder solid composition was tested in an in vivo pharmacokinetic study on rats compared to the hydroalcoholic Bergamot fruit extract. The results of the study, reported in the examples, clearly show the increase of the bioavailability of the active ingredients of Bergamot fruit extract when administered as compositions of the invention.

A preliminary clinical study on volunteers was also performed to evaluate the cholesterol lowering effect of the composition of the invention compared to the hydroalcoholic Bergamot fruit extract.

The following examples further describe the invention.

EXAMPLES

Example 1—Preparation of a Lecithin Based Powder Solid Composition of a Hydroalcoholic Extract of Bergamot Fruit 350 g of hydroalcoholic extract of Bergamot fruit, 420 g of sunflower lecithin and 70 g of maltodextrin are suspended in 8500 mL of ethyl alcohol in a reactor. The suspension is heated at 70° C. for 2 hours under mixing.

Solvent is then removed under vacuum (about 200 mBar) at 70° C. until a soft mass is obtained.

Drying is completed in an oven under vacuum at 50° C. for about 12 hours until a dry mass is obtained.

The dry mass is calibrated through a 2 mm screen and mixed with 2% of silicon dioxide to obtain a freely flowable powder.

Example 2—Preparation of a Lecithin Based Powder Solid Composition of a Hydroalcoholic Extract of Bergamot Fruit Containing an Additional Surfactant 500 g of hydroalcoholic extract of Bergamot fruit, 700 g of sunflower lecithin and 50 g of sucrose monopalmitate are solubilized in about 10 Lt of ethyl acetate in a reactor.

100 g of microcrystalline cellulose are added to the obtained solution and the suspension is heated at 70° C. for 2 hours under mixing.

Solvent is then removed under vacuum (about 200 mBar) at 70° C. until a soft mass is obtained.

Drying is completed in an oven under vacuum at 50° C. for about 12 hours until a dry mass is obtained.

The dry mass is calibrated through a 2 mm screen and mixed with 2% of silicon dioxide and 1% of talc to obtain a freely flowable powder.

Example 3—Pharmacokinetic Study on Rats

Plasma concentration of naringin and neohesperidin were determined in rats after the oral administration of a single dose of the composition obtained in Example 1 and compared to the plasma concentration obtainable administering the hydroalcoholic extract of Bergamot fruit. Male Sprague-Dawley rats, weighting about 300 g were used for the pharmacokinetic experiments. A single dose of 500 mg/Kg of hydroalcoholic extract of Bergamot fruit and a single dose of 500 mg/Kg of the composition of obtained in example 1, corresponding to about 200 mg/Kg of hydroalcoholic extract of Bergamot fruit, were administered as water suspension by intragastric gavage. Blood sample were collected after 1 and 2 hours from the administration. Plasma was obtained from blood samples by centrifugation at 2.000 rpm for 10 minutes at 4° C. in presence of EDTA. After a suitable extraction procedure, samples were analyzed by HPLC equipped with fluorescent detector for naringin and neohesperidin concentration.

The analytical results are summarized in the following table 1:

TABLE 1

|  | Naringin (ppm) |  | Neohesperidin (ppm) |  |
| --- | --- | --- | --- | --- |
|  | Hydroalcoholic extract of Bergamot fruit | Composition of Example 1 | Hydroalcoholic extract of Bergamot fruit | Composition of Example 1 |
| Rat 1 (1 hour) | 0.2029 | 1.4409 | 0.2728 | 1.5621 |
| Rat 2 (1 hour) | 0.2286 | 1.545 | 0.2751 | 1.1917 |
| Rat 3 (1 hour) | 0.2186 | 1.7878 | 0.3201 | 1.543 |
| Rat 1 (2 hour) | 0.1089 | 1.9046 | 0.1648 | 3.5433 |
| Rat 2 (2 hour) | 0.1029 | 2.334 | 0.1447 | 3.0571 |
| Rat 3 (2 hour) | 0.1067 | 2.0516 | 0.1417 | 3.2322 |

Example 4—Formulations Containing the Composition Obtained in Example 1 (Tablets)

| Composition obtained in Example 1 | 500.0 mg |
| --- | --- |
| Microcrystalline cellulose | 150.0 mg |
| Dicalcium phosphate anhydrous | 104.0 mg |
| Sodium croscarmellose | 30.0 mg |
| Silicon dioxide | 8.0 mg |
| Magnesium stearate | 8.0 mg |

1.0 Kg of the composition obtained in Example 1, 0.3 Kg of microcrystalline cellulose (direct compression grade), 0.208 Kg of dicalcium phosphate anhydrous (direct compression grade) and 0.06 Kg of sodium croscarmellose were blended in a V-mixer for 10 minutes. 16 g of silicon dioxide and 16 g of magnesium stearate were added to the powder mixture and blended for 2 additional minutes. The obtained mixture was compressed in a single punch tabletting machine, equipped with a round concave punch with a diameter of 11 mm.

Example 5—Formulations Containing the Composition Obtained in Example 2 (Size 0 Hard Gelatin Capsules)

| Composition obtained in example 2 | 350.0 mg |
| --- | --- |
| Silicon dioxide | 5.0 mg |
| Magnesium stearate | 5.0 mg |

2.0 Kg of the composition obtained in example 2 were blended with 28.5 g of silicon dioxide and 28.5 g of magnesium stearate in a V-mixer for 2 minutes. The mixture was filled in size 0 hard gelatin capsules.

Example 6—Clinical Study

A pilot clinical study on volunteers was also performed to evaluate the cholesterol lowering effect of the composition of the invention.

Ten (10) patients were treated with 2 hard gelatin capsules of 500 mg, one in the morning and one in the evening (for a total of 1000 mg daily) for 30 consecutive days. The primary objective of the study was the evaluation of the clinical activity on the reduction of cardiovascular risk in patients with dyslipidemia associated or not with hyperglycemia, by measuring the modulation of total cholesterol (tChol), low-density lipoproteins (LDL), triglycerides (TG), high-density lipoproteins (HDL) and blood glucose before and after 30-day treatment. Safety was also assessed.

Inclusion criteria were: signed informed consent; age between 30 and 90 years old; a diagnosis of type II diabetes mellitus; fasting blood glucose≥110 mg/dl; isolated hypercholesterolemia (cholesterol bound to low-density lipoprotein cLDL≥130 mg/dl), with or without hypertriglyceridemia (>175 mg/dl); medium cardiovascular risk measured by the "European Guidelines on Cardiovascular disease prevention on clinical practice" (2012). All concomitant treatments must have begun at least 3 months before the beginning of the study and maintained in a constant regimen for the entire duration of the study.

The exclusion criteria were: patients with overt liver disease, serious gastrointestinal disorders, chronic renal failure, hypercalcemia, myopathy, uncontrolled diabetes, myocardial ischemic, presence of heart failure NYHA class III and IV, alcohol abuse, history of psychiatric disorders and major depression, HIV or serious infections or neoplasia, statin therapy stabilized by 4 months.

The patients were visited every 7 days during the study and the compliance was monitored. Serum aspartate aminotransferase, alanine aminotransferase, creatine were measured in order to monitor possible side effects, Treatment with 1000 mg daily for 30 consecutive days resulted in a strong reduction for total cholesterol, LDL, TG, fasting blood glucose and a significant increase in HDL in majority of subjects. The results are reported in Table 2.

The initial mean values of 277 mg/dl tChol, 184 mg/dl LDL and 255 mg/dl TG, decreased to 195, 113 and 164 mg/dl, respectively after treatment.

In addition, a reduction in fasting blood glucose was also observed.

TABLE 2

| mg/dl | tChol | | Trigl | | LDL | | HDL | | Gly | |
|---|---|---|---|---|---|---|---|---|---|---|
| | before | after | before | after | before | after | before | after | before | after |
| Mean | 277 | 195 | 255 | 164 | 184 | 113 | 41 | 50 | 111 | 101 |
| SD | 15 | 11 | 24 | 11 | 15 | 10 | 2 | 15 | 8 | 3 |

The invention claimed is:

1. A powder solid composition comprising at least one phospholipid and a hydroalcoholic extract of Bergamot fruit containing flavonoids, neoeriocitrin, naringin and neohesperidin as the only extract.

2. The powder solid composition according to claim 1, wherein the at least one phospholipid is selected from the group consisting of lecithins from soy, sunflower or egg, phosphatidyl choline, phosphatidyl serine, phosphatidyl ethanolamine, wherein the acyl groups being the same or different are mostly derived from palmitic, stearic, oleic, linoleic, linolenic acids; or combinations thereof.

3. The powder solid composition according to claim 1, wherein the at least one phospholipid is lecithin.

4. The powder solid composition according to claim 3, further comprising an additional surfactant, other than lecithin, with an HLB value equal or higher than 12.

5. The powder solid composition according to claim 4, wherein the additional surfactant is selected from the group consisting of sucrose esters, polysorbates, polyoxyethylene castor oil derivatives, polyoxyethylene stearates, D-α-tocopheryl polyethylene glycol succinate, or combinations thereof.

6. The powder solid composition according to claim 4, wherein the additional surfactant is selected from sucrose esters and D-α-tocopheryl polyethylene glycol succinate.

7. A pharmaceutical, nutraceutical or cosmetic formulation comprising a powder solid composition according to claim 1 as the only active ingredient and at least one physiologically acceptable excipient and/or carrier.

8. The pharmaceutical, nutraceutical or cosmetic formulation according to claim 7, formulated for oral administration or for topical administration.

* * * * *